(12) United States Patent
Biermann et al.

(10) Patent No.: US 6,471,519 B1
(45) Date of Patent: Oct. 29, 2002

(54) BONE SUBSTITUTE FOR TRAINING AND TESTING AND METHOD FOR MAKING

(75) Inventors: Paul J. Biermann, Columbia, MD (US); Jack C. Roberts, Columbia, MD (US); John A. Ecker, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/659,219

(22) Filed: Sep. 11, 2000

Related U.S. Application Data

(62) Division of application No. 08/825,192, filed on Mar. 27, 1997, now Pat. No. 6,116,911.

(51) Int. Cl.[7] .............................. G09B 23/28; A61F 2/28
(52) U.S. Cl. ..................................... 434/274; 623/16.11
(58) Field of Search ........................... 623/16.11, 23.61, 623/23.58, 23.59, 23.6; 528/950; 434/274

(56) References Cited

U.S. PATENT DOCUMENTS

| | | | | |
|---|---|---|---|---|
| 3,662,405 A | * | 5/1972 | Bortz et al. ..................... 501/1 |
| 4,106,219 A | * | 8/1978 | Schneider et al. ........... 434/274 |
| 4,662,888 A | * | 5/1987 | Field ........................ 623/18.11 |
| 5,314,492 A | * | 5/1994 | Hamilton et al. ......... 623/23.34 |

* cited by examiner

*Primary Examiner*—Corrine McDermott
*Assistant Examiner*—William H. Matthews
(74) *Attorney, Agent, or Firm*—Francis A. Cooch

(57) ABSTRACT

A bone substitute that drills and cuts like bone for use in training and testing comprising an inner core of a foamable polymer or other soft material and an outer shell of a polymer such as an epoxy resin with a particulate filler such as aluminum oxide or silicon carbide added thereto together with, in some cases, titanium oxide to form a slurry for casting or molding around the inner core. Also provided is a method for making the bone substitute.

3 Claims, 2 Drawing Sheets

BONE SUBSTITUTE FOR TRAINING AND TESTING AND METHOD FOR MAKING

CROSS-REFERENCE TO RELATED APPLICATION

This is a divisional of prior filed application Ser. No. 08/825,192, filed Mar. 27, 1997 now U.S. Pat. No. 6,116,911.

STATEMENT OF GOVERNMENTAL INTEREST

This invention was made with Government support under Contract No. N00039-94-C-0001 awarded by the Department of the Navy. The Government has certain rights in the invention.

BACKGROUND OF THE INVENTION

The invention relates in general to substitutes for bone, and, in particular, to a bone substitute that has the look and feel, and cutting and drilling properties of human bone thereby making it especially useful as a bone model for teaching and training medical students and for testing surgical equipment.

Drilling bone to permit use of internal screws for fixation of fractures, to implant artificial joints, to fix intramedullary implants and to utilize various other procedures is a widespread and important surgical technique. Obviously, the above surgical procedures involve precise cuts and drilling of sensitive tissues.

Unfortunately, there is a shortage of human bone tissue on which to practice new techniques and procedures. Cadaver bone is difficult and often expensive to obtain and is a serious potential biohazard as well. Currently, surgeons practice new drilling techniques on blocks of plastic or polyurethane, assuming this material closely mimics the drilling behavior of live human bone which, however, is not the case.

Previous studies on the drilling of bone have focused on orthogonal cutting and machining, and wear of machine parts, but there is currently no easy way to comprehend data concerning distinguishing drilling behavior of materials for comparison. In any event, what is needed are new materials which when molded will drill and cut like bone in order to provide better training for medical students and more realistic testing for surgical equipment manufacturers.

SUMMARY OF THE INVENTION

The invention provides a bone substitute whose properties closely mimic real bone when drilled or cut and comprises an inner core comprising a foamable polymer or other soft material to mimic cancellous bone and an outer shell formed around the inner core to mimic compact bone. The outer shell comprises a polymer such as an epoxy resin and a particulate filler such as a mineral added thereto to form a slurry for casting or molding around the inner core.

The particulate filler, which hardens the bone substitute and reduces the amount of polymer required, includes, but is not limited to, hydroxyapatite, aluminum oxide ($Al_2O_3$), silicon carbide (SiC) or mullite. For even better results, titanium oxide (Tio) can be added along with either $Al_2O_3$ or SiC to modify the interaction between the polymer and the mineral and thereby reduce wear on surgical tools.

In one embodiment, the outer shell comprises an epoxy resin and from 5% to 15% by weight of $Al_2O_3$ and from 20–45% by weight of TiO. In another embodiment, the outer shell comprises the epoxy resin and from 2.5% to 30% by weight of SiC and from 20% to 45% by weight of TiO.

To make a bone of the invention the first step is to make a female mold from an original (human) bone part. Then a bone substitute part is created from the female mold and reduced by a uniform thickness. A mold is created from the bone substitute part to replicate an inner core of the bone substitute; the inner core is then molded from a foamable polymer and suspended in the female mold. Finally, the outer shell is formed by pouring or injecting the epoxy resin/$Al_2O_3$ (or SiC)/TiO slurry into the female mold with the inner core suspended therein.

The resulting bone substitute drills and cuts substantially like real bone thereby providing medical students with an accurate feel during surgical training, and equipment manufacturers with an accurate hardness for testing surgical devices.

DETAILED DESCRIPTION OF THE INVENTION

Figure 1:
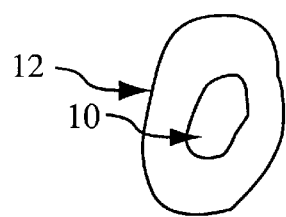
FIG. 1 illustrates a cross-section of the bone substitute of the invention.

The invention provides a bone substitute that has the look and feel, and cutting and drilling properties that closely mimic real bone. As shown in FIG. 1, the invention comprises an inner core 10 made of a foamable polymer or other soft material and an outer shell 12 comprising a polymer and a particulate filler.

The filler is to increase the hardness, toughness and/or resistance of the polymer to drilling and cutting. The polymer and particulate filler form a slurry for casting around the inner core.

In laboratory tests of the invention, discussed below, two families of epoxy resins were chosen for the polymer for ease of processing: Bisphenol A and Bisphenol F. However, other thermosetting as well as thermoplastic polymers such as those listed in Table 1 below can also be used in the invention.

TABLE 1

| | |
|---|---|
| ABS | Polyalkalene Ether |
| ABS/PA | Polyallomer |
| ABS/PC | Polyamide (Nylon) |
| ABS/PVC | Polybutadiene |
| Acetal | Polybutylene |
| Acrylic | Polycarbonate |
| Acrylonitrile Copolymer | Polyester (Saturated) |
| Alkyd | Polyester (Unsaturated) |
| Allylic Esters or Allyls (DAP,DAIP) | Polyether, chlorinated |
| ASA (Acrylic-styrene-acrylonitrile) | Polyethylene |
| Bis-maleimides | Polyimide (Polyamide-imide) |
| Cellulosics | Polyphenylene Sulfide |
| Cyanate/Cyanamide | Polypropylene |
| Epoxy | Polystyrene |
| Ethylene Vinyl Acetate | Polysulfone |
| Fluorocarbon Polymers : | Polyurethane |
| Fluorinated Ethylene-Propylene (FEP) | Polyvinyl Acetate |

TABLE 1-continued

| | |
|---|---|
| Perfluoroalkoxy (PFA) | Polyvinyl Chloride |
| Polychlorotrifluoroethylene (CTFE) | Polyvinylidene Chloride |
| Polytetrafluoroethylene (TFE) | Polyxylylene |
| Polyvinylfluoride (PVF) | Silicone |
| Polyvinylidene Fluoride (PVDF) | Styrene-acrylonitrile (SAN) |
| Furan | Styrene-maleic-anhydride (SMA) |
| Ionomer | Urea-Formaldehyde |
| Melamine-Formaldehyde | Vinyl Ester |
| Phenolic | |

The particulate filler comprises a mineral, which, as noted above, hardens the bone substitute and reduces the amount of polymer required. Suitable minerals include, but are not limited to, hydroxyapatite, aluminum oxide ($Al_2O_3$), silicon carbide (SiC) and mullite.

In the laboratory tests, as discussed below, even better results were obtained by adding a second filler, titanium oxide (TiO), to either $Al_2O_3$ or SiC to modify the interaction between the epoxy resin and the mineral and thereby reduce wear on surgical tools.

In one embodiment, the outer shell comprises an epoxy resin and from 5% to 15% by weight of $Al_2O_3$ and from 20–45% by weight of TiO. In another embodiment, the outer shell comprises the epoxy resin and from 2.5% to 30% by weight of SiC and from 20% to 45% by weight of Tio. Best results were obtained with particle size for the $Al_2O_3$ being 100 microns or less and for the SiC being 10 microns or less.

To fabricate a bone substitute of the invention the first step is to make a female mold from an original (human) bone part. Then a bone substitute part is created from the female mold and reduced by a uniform thickness. A mold is created from the bone substitute part to replicate an inner core of the bone substitute; the inner core is then molded from a foamable polymer and suspended in the female mold. Finally, the outer shell is formed by pouring or injecting, for example, the epoxy resin/$Al_2O_3$ (or SiC)/TiO slurry into the female mold with the inner core suspended therein.

As shown in Table 2, different composite samples were formed in laboratory tests, consisting of three different epoxy resin systems, EPON® Resins 815, 826 and 862 (EPON is a registered trademark of Shell Chemical Company).

TABLE 2

Composition Table

| Resin | Filler A | Filler B | Sample No. | Test Date (Drilling) |
|---|---|---|---|---|
| 826/V-40 | None | None | 7 | 19-Nov-96 |
| 815/V-40 | None | None | 8 | 19-Nov-96 |
| 826/V-40 | 35% 325 Mullite | None | 11 | |
| 826/V-40 | 56.6% 325 Mullite | None | 12 | |
| 815/V-40 | 40% 325 Mullite | None | 13 | |
| 815/V-40 | 40% 325 Mullite | None | 13 | 21-Nov-96 |
| 815/V-40 | 60.8% 325 Mullite | None | 14 | |
| 815/V-40 | 60.8% 325 Mullite | None | 14 | 21-Nov-96 |
| 862/3274 | 51.7% 100 Mullite | None | 15 | |
| 862/3274 | 51.7% 100 Mullite | None | 15 | 21-Nov-96 |
| 862/3274 | 64.6% 100 Mullite | None | 16 | |
| 862/3274 | 64.6% 100 Mullite | None | 16 | 21-Nov-96 |
| 815/V-40 | 47% 100 Mullite | None | 17 | |
| 815/V-40 | 47% 100 Mullite | None | 17 | 21-Nov-96 |
| 815/V-40 | 62% 100 Mullite | None | 18 | |
| 815/V-40 | 62% 100 Mullite | None | 18 | 21-Nov-96 |
| 826/V-40 | 24% 100 Mullite | None | 19 | |
| 826/V-40 | 62% 100 Mullite | None | 19 | 21-Nov-96 |
| 826/V-40 | 49% 100 Mullite | None | 20 | |
| 826/V-40 | 49% 100 Mullite | None | 20 | 21-Nov-96 |
| 826/V-40 | 34.2% T64-60 | None | 21 | |
| 826/V-40 | 34.2% T64-60 | None | 21 | 21-Nov-96 |
| 826/V-40 | 52% T64-60 | None | 22 | |
| 826/V-40 | 52% T64-60 | None | 22 | 21-Nov-96 |
| 815/V-40 | 61% T64-60 | None | 23 | |
| 815/V-40 | 61% T64-60 | None | 23 | 21-Nov-96 |
| 815/V-40 | 38.7% T64-60 | None | 24 | |
| 815/V-40 | 38.7% T64-60 | None | 24 | 21-Nov-96 |
| 862/3274 | 71.7% T64-60 | None | 25 | |
| 862/3274 | 71.7% T64-60 | None | 25 | 21-Nov-96 |
| 862/3274 | 52% T64-60 | None | 26 | 22-Nov-96 |
| 826/V-40 | 57% T64-200 | None | 27 | 22-Nov-96 |
| 826/V-40 | 42% T64-200 | None | 28 | 22-Nov-96 |
| 815/V-40 | 43.3% T64-200 | None | 29 | 22-Nov-96 |
| 862/3274 | 55% T64-200 | None | 30 | 22-Nov-96 |
| 862/3274 | 65% T64-200 | None | 31 | 22-Nov-96 |
| 862/3274 | 71% AC99-325 Ll | None | 32 | 22-Nov-96 |
| 862/3274 | 60.6% AC99-325 Ll | None | 33 | 22-Nov-96 |
| 815/V-40 | 50% AC99-325 Ll | None | 34 | 22-Nov-96 |
| 815/V-40 | 61% AC99-325 Ll | None | 35 | 22-Nov-96 |
| 826/V-40 | 24.7% AC99-325 Ll | None | 36 | 22-Nov-96 |
| 826/V-40 | 48% AC99-325 Ll | None | 37 | 22-Nov-96 |
| 862/3274 | 52.3% A10 ung (?) | None | 38 | 22-Nov-96 |
| 862/3274 | 40.4% A10 ung (?) | None | 39 | 22-Nov-96 |
| 815/V-40 | 30% A, 10 µm | None | 40 | 3-Dec-96 |
| 815/V-40 | 15% A, 10 µm | None | 41 | 3-Dec-96 |

TABLE 2-continued

Composition Table

| Resin | Filler A | Filler B | Sample No. | Test Date (Drilling) |
|---|---|---|---|---|
| 826/V-40 | 39% A, 10 μm | None | 42 | 3-Dec-96 |
| 826/V-40 | 10.75% A, 10 μm | None | 43 | 3-Dec-96 |
| 826/V-40 | 29% Premalox | None | 44 | 3-Dec-96 |
| 826/V-40 | 46% Premalox | None | 45 | 3-Dec-96 |
| 815/V-40 | 50% Premalox | None | 46 | 3-Dec-96 |
| 815/V-40 | 39.8% Premalox | None | 47 | 3-Dec-96 |
| 862/3274 | 31.6% Premalox | None | 48 | 3-Dec-96 |
| 862/3274 | 55.5% Premalox | None | 49 | 3-Dec-96 |
| 862/3274 | 10.24% Q-Cel 2116 | None | 50 | 3-Dec-96 |
| 862/3274 | 5.43% Q-Cel 2116 | None | 51 | 3-Dec-96 |
| 862/3274 | 42.3% $TiO_2$ | None | 52 | 3-Dec-96 |
| 862/3274 | 56% $TiO_2$ | None | 53 | 3-Dec-96 |
| 862/3274 | 25.5% $TiO_2$ | None | 54 | 3-Dec-96 |
| 826/V-40 | 58.2% AC99-100 | None | 55 | 3-Dec-96 |
| 815/V-40 | 33.5% 3μ SiC | None | 56 | 3-Dec-96 |
| Sawbones | None | None | 58 | 5-Dec-96 |
| 815/V-40 | 54% 3μ SiC | None | 59 | 6-Dec-96 |
| 826/V-40 | 5.6% 3μ SiC | None | 60 | 6-Dec-96 |
| 826/V-40 | 29% 3μ SiC | None | 61 | 6-Dec-96 |
| 862/3274 | 32% 3μ SiC | None | 62 | 6-Dec-96 |
| 862/3274 | 46.5% 3μ SiC | None | 63 | 19-Nov-96 |
| 826/V-40 | 27.5% AC99-100 | None | 64 | 6-Dec-96 |
| 862/3274 | 59.85% AC99-100 | None | 65 | 6-Dec-96 |
| 862/3274 | 69.5% AC99-100 | None | 66 | 6-Dec-96 |
| 815/V-40 | 48% AC99-100 | None | 67 | 6-Dec-96 |
| 815/V-40 | 64% AC99-100 | None | 68 | 6-Dec-96 |
| 826/V-40 | 16.8% 20μ SiC | None | 69 | 6-Dec-96 |
| 826/V-40 | 44.8% 20μ SiC | None | 70 | 6-Dec-96 |
| 826/V-40 | 26.4% $TiO_2$ | 5.6% α $Al_2O_3$, 0.3μ | 71 | 6-Dec-96 |
| 815/V-40 | 56% 20μ SiC | None | 72 | 6-Dec-96 |
| 815/V-40 | 33% 20μ SiC | None | 73 | 6-Dec-96 |
| 862/3274 | 55.6% 20μ SiC | None | 75 | 6-Dec-96 |
| 862/3274 | 67.3% 20μ SiC | None | 76 | 6-Dec-96 |
| 862/3274 | 53.3% 100μ SiC | None | 77 | 6-Dec-96 |
| 862/3274 | Neat Resin | None | 78 | 9-Dec-96 |
| 862/3274 | 48.68% $TiO_2$ | 7.5% α $Al_2O_3$ | 79 | 9-Dec-96 |
| 862/3274 | 45.71% $TiO_2$ | None | 80 | 10-Dec-96 |
| 862/3274 | 48.63% $TiO_2$ | 8.17% 3μ SiC | 81 | 11-Dec-96 |
| 862/3274 | 45.24% $TiO_2$ | 14.57% 3μ SiC | 82 | 11-Dec-96 |
| 862/3274 | 48.63% $TiO_2$ | 8.17% 3μ SiC | 83 | 12-Dec-96 |
| 862/3274 | 25.23% 3μ SiC | 23.51% $TiO_2$ | 84 | 13-Dec-96 |
| 862/3274 | 31.2% $TiO_2$ | 9.92% Premalox | 85 | 13-Dec-96 |
| 862/3274 | 41.54% $TiO_2$ | 5.73% 3μ SiC | 86 | 16-Dec-96 |
| 862/3274 | 42.44% $TiO_2$ | 3.82% 3μ SiC | 87 | 16-Dec-96 |
| 862/3274 | 30.72% $TiO_2$ | 9.18% Premalox | 88 | 16-Dec-96 |

Except in two cases, each sample was filled with a variety of particulate minerals and titanium oxide (together fillers) of different diameters, and different volume concentrations as shown in Table 3. Samples made were 1"×6"×⅛" in size, and were allowed to cure for a minimum of two days before any experiments were performed.

TABLE 3

| Filler | Diameter | % | Resin | Curing Agent | Treatment |
|---|---|---|---|---|---|
| A-10 Ung Alumina Oxide | 100 μm | 15.03 29.9 | EPON 815 | EPON V-40 | Cure Rm. Temp. overnight |
| | | 10.75 38.98 | EPON 826 | EPON V-40 | Blow Dry, Cure Rm. Temp. |
| | | 40.39 52.33 | EPON 862 | EPICURE 3274 | |
| Premalox 10 SG Alumina Oxide | 0.25 μm | 28.64 45.87 | EPON 826 | EPON V-40 | Cure Rm. Temp. overnight |
| | | 39.83 50.65 | EPON 815 | EPON V-40 | Cure Rm. Temp. overnight |
| | | 31.58 55.54 | EPON 862 | EPICURE 3274 | Blow Dry, Cure 150° F. 2 hrs |
| Mullite 100 Mesh | ~149 μm | 24.02 48.97 | EPON 826 | EPON V-40 | Blow Dry, Cure 150° F. 1 hr |
| | | 46.98 62.4 | EPON 815 | EPON V-40 | Blow Dry, Cure Rm. Temp. overnight |
| | | 51.66 64.62 | 862 | EPICURE 3274 | Blow Dry, Cure Rm. Temp. overnight |

TABLE 3-continued

| Filler | Diameter | % | Resin | Curing Agent | Treatment |
|---|---|---|---|---|---|
| Mullite 325 Mesh | ~44 μm | 34.91 56.62 | EPON 826 | EPON V-40 | Blow Dry, cure Rm. Temp. overnight |
| | | 39.69 60.8 | EPON 815 | EPON V-40 | Blow Dry, Cure Rm. Temp. overnight |
| | | 41.96 62.93 | EPON 862 | EPICURE 3274 | Blow Dry, Cure rm. Temp. overnight |
| Aluchem AC99-100 Tabular Alumina | ~149 μm | 27.5 58.28 | EPON 826 | EPON V-40 | Blow Dry, Cure 150° F. 2 hrs |
| | | 48.19 64.1 | EPON 815 | EPON V-40 | Cure Rm. Temp. overnight |
| | | 59.85 69.46 | EPON 862 | EPICURE 3274 | Blow Dry, Cure Rm. Temp overnight |
| AC99-325 L1 Tab. Alumina Ground Low Iron | ~44 μm | 24.71 47.99 | EPON 826 | EPON V-40 | Blow Dry, Cure Rm. Temp overnight |
| | | 50.18 61.58 | EPON 815 | EPON V-40 | Blow Dry, Cure 15° F. 3 um |
| | | 60.61 71.15 | EPON 862 | EPICURE 3274 | Blow Dry, Cure Rm. Temp. overnight |
| T64-60 Tabular Alumina | 100 μm | 34.24 52.05 | EPON 826 | EPON V-40 | Blow Dry, Cure 150° F. 2.5 hrs. |
| | | 38.68 61.19 | EPON 815 | EPON V-40 | Blow Dry Cure rm. Temp overnight |
| | | 52.05 71.77 | EPON 862 | EPICURE 3274 | Blow Dry, Cure 150° F. 3 hrs |
| Silicon Carbide | 3 μm | 5.64 29.05 | EPON 826 | EPON V-40 | Cure Rm. Temp. overnight |
| | | 31.9 46.51 | EPON 862 | EPI-CURE 3274 | Blow Dry, Cure 150° F. 2 hrs |
| | | 33.52 54.1 | EPON 815 | EPON V-40 | Blow Dry, Cure Rm. Temp. overnight |
| Silicon Carbide | 100 μm | 44.06 62.35 | EPON 882 | EPI-CURE 3274 | Blow Dry, Cure 150° F. 3 hrs |
| | | 38.24 53.33 | EPON 815 | EPON V-40 | Blow Dry, cure 150° F. 2 hrs. |
| | 20 μm | 32.74 56.29 | EPON 815 | EPON V-40 | Blow Dry, Cure 150° F. 3.5 hrs. |
| | | 16.79 44.8 | EPON 826 | EPON V-40 | Blow Dry, Cure Rm. Temp. overnight |
| | | 55.6 67.31 | EPON 862 | EPI-CURE 3274 | Blow Dry, Cure Rm. Temp. overnight |
| Titanium (IV) Oxide | | 25.55 43.54 | EPON 862 | EPI-CURE 3274 | Blow Dry, Cure rm. Temp. overnight |
| | | 42.3 56.2 | | | Cure Rm. Temp. overnight |
| Same (Dried 150° F. 2 hrs) | | 47.57 65.71 | EPON 862 | EPICURE 3274 | Cure Rm. Temp. overnight |
| | | 25.77 61.29 | EPON 826 | EPON V-40 | Cure Rm. Temp. overnight |
| | | 56.8 71.17 | EPON 815 | EPON V-40 | Cure Rm. Temp. overnight |
| Q-Cell 2116 | | 5.43 10.24 | EPON 862 | EPICURE 3274 | Blow Dry, Cure Rm. Temp overnight |
| T64-200 Tabular Alumina | 20 μm | 55.12 64.88 | EPON 862 | EPICURE 3274 | Blow Dry, Cure Rm. Temp. overnight |
| | | 43.32 67.85 | EPON 815 | EPON V-40 | Blow Dry, Cure Rm. Temp. overnight |
| T64-200 Tabular Alumina | | 41.89 57 | EPON 826 | EPON V-40 | Blow Dry, Cure Rm. Temp. overnight |

Bone specimens tested for comparison were bovine, lamb and dog, the bovine and lamb obtained from a local store, kept cold, and used within one week. The length of time the canine bone had been frozen was unknown. Bovine bone tissue has previously been shown to be similar to human bone tissue with respect to many physical and structural properties. Also tested was a bone substitute product manufactured by Pacific Research Laboratories, Inc., called Sawbones®.

A standard surgical drill, the Maxidriver, was obtained and used for all drilling tests. A standard ⅛" twist drill bit was used, a new bit for each sample. The drill was driven by nitrogen gas and all tests were performed at 110 psi, which results in a speed of approximately 900 rpm. The drill was clamped to the bottom of an INSTRON tensile machine, and samples were attached to a load cell and lowered onto the rotating drill.

Data was recorded for a given feed rate (usually two in/min) and fed to a personal computer. Information retrieved was load versus percent extension. A minimum of six holes were drilled in each sample with the same drill bit. A new drill bit was used for each bone or composite sample.

Figure 2:
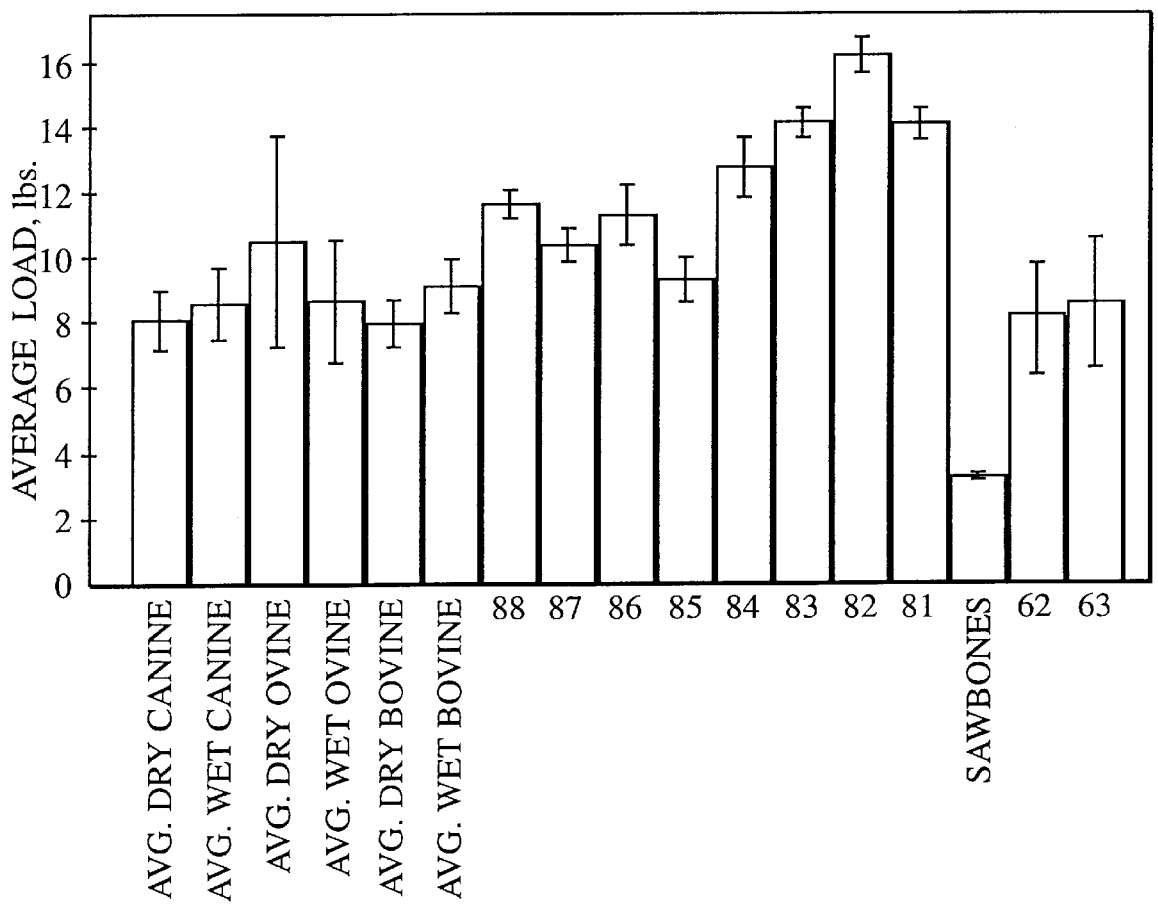
FIG. 2 is a bar graph illustrating drilling data from dog, lamb and cow bones and various compositions of bone substitutes of the invention.
Figure 3:
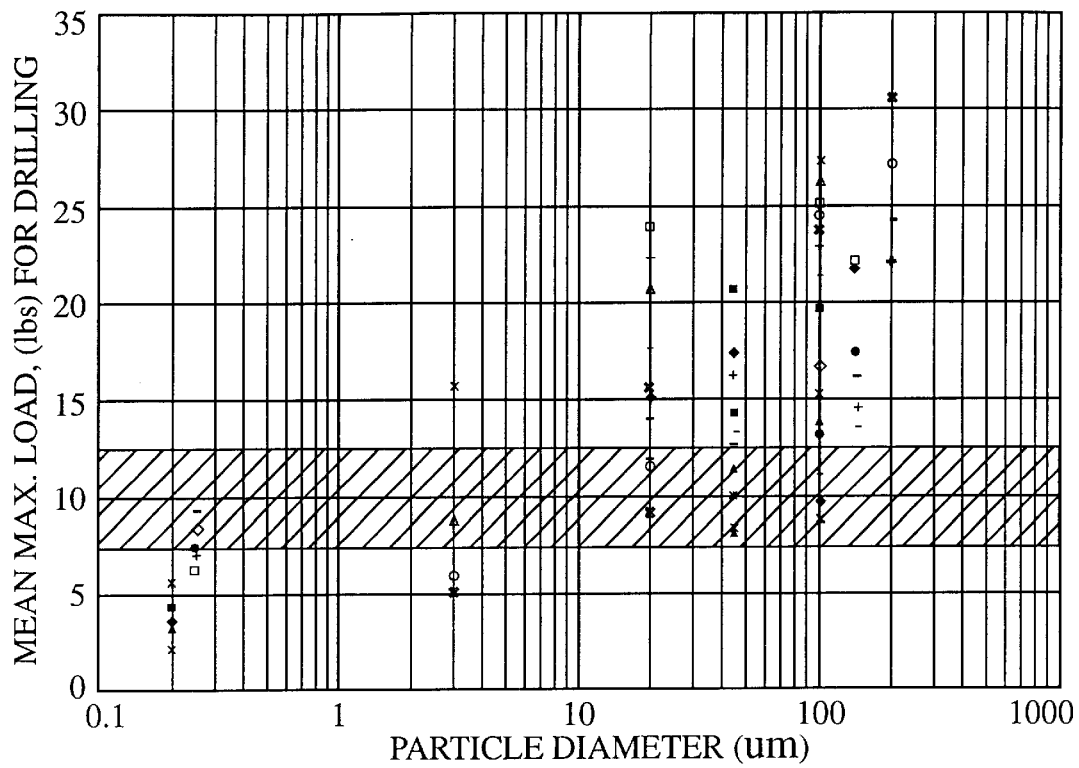
FIG. 3 is a chart showing load as a function of particle diameter for different substances added to an epoxy resin comprising the outer shell of the invention.

FIG. 2 provides comparative results between the dog, lamb and cow samples, the Sawbones® sample and ten samples of the invention (the sample numbers refer to the numbers in Table 2). FIG. 3 with its accompanying legend illustrates in chart form the performance of each sample from Table 2 as a function of filler particle diameter. The area where real bone falls is indicated by the hash marked area between approximately 7.5 and 12.5 on the load or y-axis. The legend can be used in conjunction with Table 4 to determine the performance of each sample.

TABLE 4

|  | 862/3274 | % | 826/V-40 | % | 815/V-40 | % | 826/3234 | % |
|---|---|---|---|---|---|---|---|---|
| $TiO_2$ | A1 | 42.3 | B1 | 45.5 |  |  | C1 | 54.71 |
|  | A2 | 56 |  |  |  |  |  |  |
|  | A3 | 25.5 |  |  |  |  |  |  |
| Premalox | F1 | 31.6 | D1 | 29 | E1 | 50 |  |  |
|  | F2 | 55.5 | D2 | 46 | E2 | 39.8 |  |  |
| SiC-3 um | I1 | 32 | H1 | 29 | G1 | 33.5 |  |  |
|  | I2 | 46.5 | H2 | 32 | G2 | 54 |  |  |
| SiC-20 um | P1 | 55.6 | N1 | 16.8 | O1 | 56 |  |  |
|  | P2 | 67.3 | N2 | 44.8 | O2 | 33 |  |  |
| T64-200 | M1 | 55 | K1 | 57 | L1 | 43.3 |  |  |
|  | M2 | 65 | K2 | 42 |  |  |  |  |
| Mullite-325 | Q1 | 63 | R1 | 35 | S1 | 40 |  |  |
|  | Q2 | 42 | R2 | 56.5 | S2 | 60.8 |  |  |
| AC99-325 Ll | T1 | 71 | V1 | 24.7 | U1 | 50 |  |  |
|  | T2 | 60.6 | V2 | 48 | U2 | 61 |  |  |
| Mullite-100 | W1 | 51.7 | Y1 | 24 | X1 | 47 |  |  |
|  | W2 | 64.6 | Y2 | 49 | X2 | 62 |  |  |
| T64-60 | BB1 | 71.7 | Z1 | 34.2 | AA1 | 61 |  |  |
|  | BB2 | 52 | Z2 | 52 | AA2 | 38.7 |  |  |
| A10-Ung | CC1 | 52.3 | EE1 | 39 | DD1 | 30 |  |  |
|  | CC2 | 40.4 | EE2 | 10.8 | DD2 | 15 |  |  |
| SIC-100 um |  |  |  |  | FF1 | 53.3 |  |  |
| AC99-100 | HH1 | 59.85 | GG1 | 58.2 | II1 | 48 |  |  |
|  | HH2 | 69.5 | GG2 | 27.5 | II2 | 64 |  |  |
| Sand | KK1 | 66 | LL1 | 61.3 | JJ1 | 70 |  |  |
|  | KK2 | 47.5 | LL2 | 25.8 | JJ2 | 56.8 |  |  |

Finally, Table 5 excerpts the best performing combination of epoxy resin, mineral and, in some cases TiO, for forming the outer shell of the substitute bone of the invention.

TABLE 5

| Resin (resin/hardner) | Filler 1 (weight %) | (test data) | Filler 2 (weight %) | (test data) | Table 2 Sample Nos. |
|---|---|---|---|---|---|
| Shell Epon 815/V40 | 35%–60% | 39%–50% 0.25 um $Al_2O_3$ | none |  | 46, 47 |
| 100/44 pbw | 30%–35% | 33.5% 3.0 um SiC | none |  | 56 |
|  | 60%–65% | 61% 100 um T64-60 tabular $Al_2O_3$ | none |  | 23 |
|  | 25%–35% | 30% 10 um A-10 $Al_2O_3$ | none |  | 40 |
| Shell Epon 826/V40 | 35%–60% | 35%–56.6% 44 um mullite | none |  | 11, 12 |
| 100/100 pbw | 20%–35% | 24% 100 um mullite | none |  | 19 |
|  | 20%–55% | 24.7%–48% 44 um AC99-325 ground tabular $Al_2O_3$ | none |  | 36, 37 |
|  | 25%–35% | 29% 0.25 um $Al_2O_3$ | none |  | 44 |
|  | 10%–50% | 16.8%–44.8% 20 um SiC | none |  | 69, 70 |
| Shell Epon 862/3274 | 35%–55% | 40.4%–52.3% 10 um A-10 $Al_2O_3$ | none |  | 38, 39 |
| 100/44 pbw | 25%–40% | 31.6% 0.25 um $Al_2O_3$ | none |  | 48 |
|  | 30%–50% | 32%–46.5% 3 um SiC | none |  | 62, 63 |
|  | 5%–15% | 9.2%–9.9% 0.25 um $Al_2O_3$ | 45%–20% | 31.2%–30.7% $TiO_2$ | 85, 88 |
|  | 2.5%–30% | 3.8%–25.2% 3 um SiC | 45%–20% | 42.4%–23.5% $TiO_2$ | 84, 86, 87 |

The resulting bone substitute of the invention drills and cuts substantially like real bone thereby providing medical students with an accurate feel during surgical training, and equipment manufacturers with an accurate hardness for testing surgical devices.

We claim:

1. A bone substitute useful as a bone model for teaching and training students and for testing surgical equipment, the bone substitute comprising:
    an inner core comprising a foamable polymer; and
    an outer shell formed around the inner core, the outer shell comprising an epoxy resin and silicon carbide (SiC) added to the epoxy resin.

2. A bone substitute useful as a bone model for teaching and training students and for testing surgical equipment, the bone substitute comprising:
    an inner core comprising a foamable polymer; and
    an outer shell formed around the inner core, the outer shell comprising a polymer, and silicon carbide (SiC) and titanium oxide (TiO) added to the polymer to form a slurry for casting or molding around the inner core, said bone substitute exhibiting properties substantially like real bone useful for training and testing.

3. A bone substitute comprising:

an inner core comprising a foamable polymer; and an outer shell formed around the inner core, the outer shell comprising an epoxy resin and from 2.5% to 30% by weight of silicon carbide (SiC) and from 20% to 45% by weight of titanium oxide (TiO) added to the epoxy resin to form a slurry for casting or molding around the inner core, said bone substitute exhibiting properties substantially like real bone useful for training and testing.

* * * * *